United States Patent
Kataoka

(10) Patent No.: US 11,412,925 B2
(45) Date of Patent: Aug. 16, 2022

(54) OPHTHALMIC IMAGING APPARATUS AND STORAGE MEDIUM

(71) Applicant: NIDEK CO., LTD., Aichi (JP)

(72) Inventor: Akira Kataoka, Aichi (JP)

(73) Assignee: NIDEK CO., LTD., Aichi (JP)

( * ) Notice: Subject to any disclaimer, the term of this patent is extended or adjusted under 35 U.S.C. 154(b) by 338 days.

(21) Appl. No.: 16/398,476

(22) Filed: Apr. 30, 2019

(65) Prior Publication Data

US 2019/0335992 A1 Nov. 7, 2019

(30) Foreign Application Priority Data

May 7, 2018 (JP) .............................. JP2018-089438

(51) Int. Cl.
  *A61B 3/10* (2006.01)
  *A61B 3/14* (2006.01)
  *A61B 3/00* (2006.01)
  *G01B 9/02091* (2022.01)

(52) U.S. Cl.
  CPC ............ *A61B 3/102* (2013.01); *A61B 3/0008* (2013.01); *A61B 3/14* (2013.01); *A61B 3/0016* (2013.01); *G01B 9/02091* (2013.01)

(58) Field of Classification Search
  CPC ......... A61B 3/10; A61B 3/102; A61B 3/0008; A61B 3/0025; A61B 3/0066; A61B 3/12; A61B 3/122514; A61B 3/0016; G01B 9/02091
  USPC .......................... 351/359, 205, 206, 246, 351
  See application file for complete search history.

(56) References Cited

U.S. PATENT DOCUMENTS

| | | | |
|---|---|---|---|
| 2010/0142780 A1* | 6/2010 | Yasuno | G01N 21/4795 382/131 |
| 2010/0226553 A1 | 9/2010 | Suehira | |
| 2017/0119242 A1 | 5/2017 | Jia et al. | |
| 2018/0028056 A1 | 2/2018 | Kubota | |
| 2019/0150729 A1* | 5/2019 | Huang | A61B 3/102 |

FOREIGN PATENT DOCUMENTS

| | | |
|---|---|---|
| JP | 2010-210267 A | 9/2010 |
| JP | 2011-92290 A | 5/2011 |
| JP | 2018-15189 A | 2/2018 |

OTHER PUBLICATIONS

Office Action dated Feb. 22, 2022, issued by the Japan Patent Office in counterpart Japanese Machine Patent Application No. 2018-089438.

* cited by examiner

*Primary Examiner* — Marin Pichler
(74) *Attorney, Agent, or Firm* — Sughrue Mion, PLLC

(57) ABSTRACT

An ophthalmic imaging apparatus includes an OCT optical system that detects an interference signal between measurement light with which a subject eye is irradiated and reference light, and acquires OCT data of the subject eye by processing the interference signal, a scanner that scans with the measurement light on a scanning line on the subject eye, and a processor. The processor determines whether or not the OCT data acquired on the scanning line is proper, controls the scanner based on a determination result to change the scanning line for the measurement light to the next scanning line, and interpolates an alternative to OCT data determined not to be proper, based on OCT data corresponding to scanning lines around a scanning line on which the OCT data determined not to be proper is acquired.

9 Claims, 4 Drawing Sheets

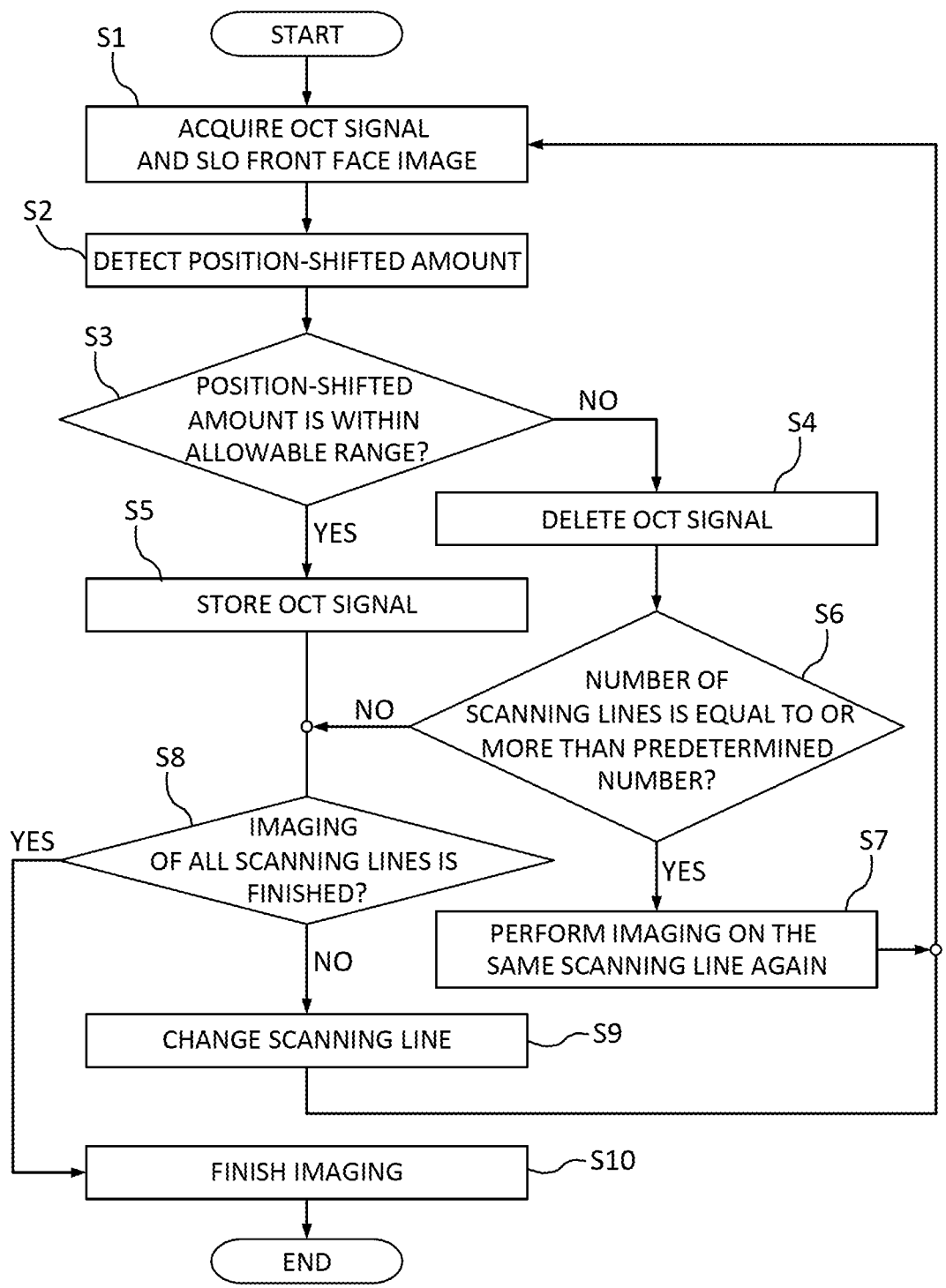

OPHTHALMIC IMAGING APPARATUS AND STORAGE MEDIUM

CROSS-REFERENCE TO RELATED APPLICATION

This application claims priority from Japanese Patent Application No. 2018-089438 filed on May 7, 2018, the entire subject-matter of which is incorporated herein by reference.

TECHNICAL FIELD

The present disclosure relates to an ophthalmic imaging apparatus and a storage medium storing an ophthalmic imaging program for imaging a subject eye.

BACKGROUND

An optical coherence tomography (OCT) using low coherent light is known as an ophthalmic imaging apparatus (for example, see JP-A-2010-210267). A tomographic image, a motion contrast image, and the like of a subject eye can be acquired with using the OCT technology.

In the ophthalmic imaging apparatus, a subject eye in a fixation state is irradiated with measurement light, and thereby the subject eye is imaged. In a case where the subject eye in the fixation state moves, the imaging may be repeated on the same scanning line. Thus, an imaging time tends to be long, and this is a burden on both an examiner and a subject (an examinee).

SUMMARY

An object of the present disclosure is to provide an ophthalmic imaging apparatus and a storage medium storing an ophthalmic imaging program in which it is possible to acquire OCT data of a subject eye with high efficiency and to reduce a burden on a subject.

In order to achieve the above object, the present disclosure includes the following configurations.

(1) An ophthalmic imaging apparatus that acquires OCT data of a subject eye, including:
an OCT optical system configured to detect an interference signal between measurement light with which the subject eye is irradiated and reference light;
a scanner configured to scan with the measurement light on a scanning line on the subject eye; and
a processor configured to:
determine whether or not the OCT data acquired on the scanning line is proper;
control the scanner based on a determination result to change the scanning line to a next scanning line; and
interpolate an alternative to OCT data determined not to be proper, based on OCT data corresponding to scanning lines around a scanning line on which the OCT data determined not to be proper is acquired.

(2) The ophthalmic imaging apparatus according to the above-described (1),
in which the processor
controls the scanner to scan with the measurement light on the same scanning line a predetermined number of times, and
changes the scanning line to the next scanning line in a case where OCT data determined to be proper is acquired or in a case where the OCT data determined not to be proper are acquired in scanning of all the predetermined number of times.

(3) The ophthalmic imaging apparatus according to the above-described (1),
in which in a case where the OCT data determined not to be proper are consecutively acquired in scanning of a predetermined number of scanning lines, the processor controls the scanner to continuously scan with the measurement light on the same scanning line until OCT data determined to be proper is acquired.

(4) The ophthalmic imaging apparatus according to the above-described (1),
in which the processor interpolates the alternative to the OCT data determined not to be proper, based on OCT data determined to be proper, which is acquired in scanning on at least any one of scanning lines before and after the scanning line on which the OCT data determined not to be proper is acquired.

(5) The ophthalmic imaging apparatus according to the above-described (1),
in which the processor is configured to:
trace and detect a movement of the subject eye; and
control the scanner based on a detection result of the movement to correct the scanning line for the subject eye,
in which in a case where a correction of the scanning line is not stably performed, the processor stops the control based on the detection result and changes the scanning line of the measurement light to the next scanning line.

(6) The ophthalmic imaging apparatus according to the above-described (1),
in which the OCT data is motion contrast data acquired by arithmetically processing the interference signal, and
the processor interpolates an alternative to motion contrast data determined not to be proper, based on motion contrast data of scanning lines around a scanning line on which the motion contrast data determined not to be proper is acquired.

(7) The ophthalmic imaging apparatus according to the above-described (6),
in which the motion contrast data is front face motion contrast data corresponding to the scanning line, and
the processor interpolates an alternative to front face motion contrast data determined not to be proper, based on front face motion contrast data of scanning lines around a scanning line on which the front face motion contrast data determined not to be proper is acquired.

(8) A non-transitory computer readable recording medium storing an ophthalmic imaging program used in an ophthalmic imaging apparatus that includes an OCT optical system configured to detect an interference signal between measurement light with which a subject eye is irradiated and reference light, and acquires an OCT image of the subject eye by processing the interference signal,
in which the ophthalmic imaging program is executed by a processor of the ophthalmic imaging apparatus to cause the ophthalmic imaging apparatus to perform:
determining whether or not OCT data acquired on a scanning line is proper;
controlling a scanner based on a determination result to change the scanning line to a next scanning line; and
interpolating an alternative to OCT data determined not to be proper, based on OCT data corresponding to scanning lines around a scanning line on which the OCT data determined not to be proper is acquired.

BRIEF DESCRIPTION OF DRAWINGS

FIG. 2 is a flowchart illustrating determination processing.

DETAILED DESCRIPTION

<Outline>

Figure 1A:
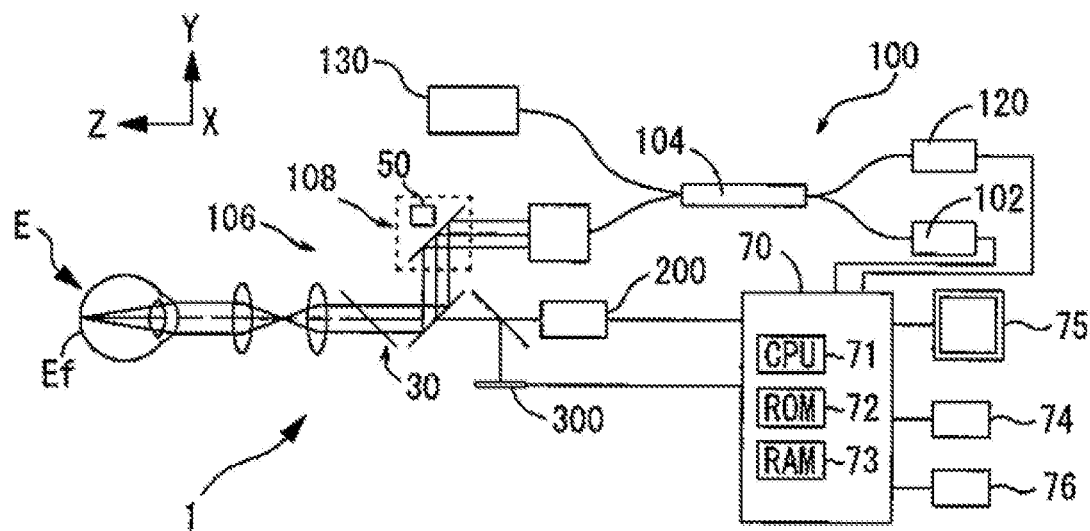
FIG. 1A is a diagram illustrating an optical system and a control system of an ophthalmic imaging apparatus.

One typical embodiment will be described with reference to the drawings. FIGS. 1A to 4 are diagrams illustrating an ophthalmic imaging apparatus according to the embodiment. The following sections classified with < > may be used independently or in association.

For example, the ophthalmic imaging apparatus (for example, an ophthalmic imaging apparatus 1) may be an optical coherence tomography (hereinafter, OCT device) that acquires OCT data of a subject eye by processing an interference signal acquired by an OCT optical system. For example, the ophthalmic imaging apparatus may be an apparatus obtained by combining a scanning laser ophthalmoscope (hereinafter, SLO device) and an OCT device. The SLO device performs two-dimensional scanning with laser light so as to acquire SLO front face image data of a subject eye. For example, the ophthalmic imaging apparatus may be an apparatus obtained by combining a treatment laser device, an OCT device, and an SLO device. The treatment laser device performs treatment on a subject eye by irradiating tissues of the subject eye with treatment laser. In the example, an ophthalmic imaging apparatus including at least an OCT optical system may be provided.

<OCT Optical System>

For example, the ophthalmic imaging apparatus according to the example includes an OCT optical system (for example, an OCT optical system 100) that detects an interference signal between measurement light with which a subject eye is irradiated and reference light. The ophthalmic imaging apparatus acquires OCT data of the subject eye by processing an interference signal. For example, the OCT optical system may include a scanner (for example, a scanner 108) that scans with measurement light on a scanning line on the subject eye. For example, the measurement light may be used for scanning in a manner of raster scanning or radial scanning. For example, the OCT optical system may include a detector (for example, a detector 120) that splits light from a light source into a measurement optical path and a reference optical path and detect an interference signal between reference light through the reference optical path and measurement light guided to the subject eye through the measurement optical path.

For example, the OCT optical system may have a Fourier domain OCT optical system as a basic configuration. As the Fourier domain OCT optical system, a spectral-domain OCT (SD-OCT) optical system may be provided. A swept source OCT (SS-OCT) optical system may be provided. For example, the OCT optical system may have a time domain OCT (TD-OCT) as a basic configuration. The technology in the present disclosure may be applied to intensity OCT that detects reflection intensity of an object, OCT angiography (for example, a Doppler OCT) that detects MC data of an object, polarization sensitive OCT (PS-OCT), and the like. The technology may be applied to multifunction OCT obtained by combining intensity OCT and PS-OCT.

<OCT Data>

The OCT data may be signal data or image data generated from signal data. For example, the OCT data may include at least any one of tomographic image data indicating reflection intensity characteristics of a subject eye, OCT angiographic data (for example, OCT motion contrast data) of the subject eye, Doppler OCT data indicating Doppler characteristics of the subject eye, and polarization characteristic data indicating polarization characteristics of the subject eye.

For example, the OCT data may include at least any one of A scan data (for example, A scan tomographic image data), B scan data (for example, B scan tomographic image data and two-dimensional OCT angiographic data), front face (En face) data (for example, OCT front face data and front face motion contrast data), and three-dimensional data (for example, three-dimensional tomographic image data and three-dimensional OCT angiographic data).

For example, the tomographic image data may be A scan tomographic image data. For example, the tomographic image data may be B scan tomographic image data. The B scan tomographic image data may be tomographic image data acquired by scanning with measurement light along a scanning line (traversing position) in any (for example, X-direction) of XY-directions. For example, the tomographic image data may be three-dimensional tomographic image data. The three-dimensional tomographic image data may be tomographic image data acquired by two-dimensional scanning with measurement light.

For example, the OCT data may be OCT front face data acquired from three-dimensional tomographic image data. The OCT front face data may include an integrated image obtained by being integrated in a depth direction, an integrated value of spectrum data at each of XY positions, luminance data at each of XY positions in a predetermined depth direction, and a retina surface image.

For example, the OCT angiographic data may be two-dimensional OCT angiographic data. The two-dimensional OCT angiographic data may be OCT angiographic data acquired by scanning with measurement light along a scanning line (traversing position) in any (for example, X-direction) of the XY-directions. For example, the OCT angiographic data may be three-dimensional OCT angiographic data. The three-dimensional OCT angiographic data may be OCT angiographic data acquired by two-dimensional scanning with measurement light. For example, the OCT angiographic data may be front face motion contrast data acquired from three-dimensional motion contrast data.

For example, in the example, the ophthalmic imaging apparatus may acquire motion contrast data acquired by arithmetically processing an interference signal, as such OCT data. In other words, a plurality of OCT signals may be acquired by the OCT optical system, and motion contrast data based on the plurality of OCT signals may be acquired by arithmetic processing.

<Determination Processing>

For example, the ophthalmic imaging apparatus according to the example may include a processor (for example, a control unit 70). The processor determines whether or not OCT data acquired on a scanning line is proper. For example, whether or not the OCT data is proper may be performed based on OCT data (at least any of signal data and image data). For example, in a case where the OCT data is signal data, the processor may determine that the OCT data is not proper, when signal intensity of the OCT signal is equal to or less than a predetermined threshold. The predetermined threshold may be set in advance by experiments, simulations, or the like, or may be randomly set. For example, in a case where the OCT data is signal data, the processor may determine that the OCT data is not proper, when the waveform of at least one of a plurality of OCT signals acquired on one scanning line is different from the waveforms of other OCT data.

For example, in a case where the OCT data is image data, the processor may determine that the OCT data is not proper, when a luminance value of the OCT image is equal to or less than a predetermined threshold. The predetermined threshold may be set in advance by experiments, simulations, or the like, or may be randomly set. For example, in a case where the OCT data is image data, the processor may determine that the OCT data is not proper, when at least one of a plurality of OCT images acquired on one scanning line is different from other images.

For example, whether or not the OCT data is proper may be performed based on data different from the OCT data. In this case, the processor may detect blink of the subject eye, the position-shifted amount of the subject eye, and the like by using an anterior ocular segment observation image of the subject eye and determine whether or not OCT data is proper, from detection results thereof. For example, when detecting blink, the processor may determine that the OCT data is not proper. For example, when the position-shifted amount of the subject eye (for example, a shifted amount of the corneal apex position) is out of an allowable range, the processor may determine that the OCT data is not proper. The allowable range may be set in advance by experiments, simulations, or the like, or may be randomly set. In this case, the processor may detect the position-shifted amount of the subject eye by using front face image data acquired by an infrared imaging optical system (for example, an SLO device and an IR camera) that images the fundus of the subject eye with infrared light. As an example, the processor may detect the position-shifted amount of the subject eye by using SLO data of the subject eye, which has been acquired by the SLO device and determine whether or not OCT data is proper, from detection results thereof. For example, the processor may determine that the OCT data is not proper, when the position-shifted amount is out of the allowable range. Front face image data of the fundus of the subject eye may be front face image data acquired by a fundus front face observation optical system that observes the front of the fundus of the subject eye. Color front face image data obtained by imaging the fundus of the subject eye with visible light may be used.

The processor may have a configuration of combining such determination processing so as to determine whether or not OCT data is proper. In other words, the processor may have a configuration of determining whether or not OCT data is proper, by at least one of the signal intensity of the OCT data, the waveform of the OCT data, the luminance value of the OCT data, the blink of the subject eye, the position-shifted amount of the subject eye, and the like. In a case where it is determined that the OCT data is not proper, the processor may determine whether or not the number of scanning lines on which this OCT data has been acquired continues by a predetermined number of scanning lines. That is, the processor may determine whether or not the number of scanning lines on which this OCT data has been acquired continues by the predetermined number of scanning lines <Control of Scanner>

The processor controls the scanner based on the determination result of the processor to change the scanning line for the measurement light to a next scanning line. For example, in a case where the processor determines that OCT data acquired on a scanning line is proper, the processor may control the scanner and change the scanning line to the next scanning line. For example, even in a case where the processor determines that the OCT data acquired on the scanning line is not proper, the processor may control the scanner and change the scanning line to the next scanning line. For example, as described above, the scanning line for the measurement light is changed regardless of whether or not OCT data acquired on each scanning line is proper, in accordance with the determination result of the processor. Thus, it is possible to reduce imaging time of the subject eye and to reduce a burden on a subject For example, the processor may control the scanner to scan with the measurement light on the same scanning line a predetermined number of times. In this case, in a case where OCT data determined to be proper by the processor is acquired, the processor may change the scanning line to the next scanning line. In this case, in a case where OCT data determined not to be proper by the processor has been acquired in scanning of all a predetermined number of times, the processor may change the scanning line to the next scanning line. For example, with such a configuration, it is possible to reduce the number of scanning lines on which OCT data determined not to be proper by the processor is acquired. Thus, the examiner can acquire an imaged image of the subject eye with high quality.

For example, the processor may control the scanner and change the scanning line of the measurement light to the next scanning line, based on a determination result obtained by determining whether or not the number of scanning lines on which OCT data determined not to be proper by the processor continues by a predetermined number of scanning lines. In this case, in a case where OCT data which are determined not to be proper and correspond to a predetermined number of scanning lines are consecutively acquired, the processor may control the scanner to continue scanning on the same scanning line with the measurement light until OCT data determined to be proper by the processor is acquired. Thus, a situation in which OCT data which are determined not to be proper and correspond to a predetermined number or more of scanning lines are consecutively acquired does not occur. Accordingly, it is possible to secure OCT data subjected to interpolation by the interpolation portion, with uniform accuracy. In a case where the situation in which OCT data which are determined not to be proper and correspond to a predetermined number or more of scanning lines are consecutively acquired does not occur, the processor may change the scanning line for the measurement light to the next scanning line.

<Interpolation Processing>

The processor interpolates an alternative to OCT data determined not to be proper, based on OCT data corresponding to scanning lines around a scanning line on which OCT data determined not to be proper by the processor has been acquired.

For example, the surrounding scanning lines may be a plurality of scanning lines provided around the scanning line on which OCT data determined not to be proper has been acquired. As an example, the surrounding scanning lines may be a plurality of scanning lines provided before the scanning line on which the OCT data determined not to be proper has been acquired, or may be a plurality of scanning lines provided after the scanning line on which the OCT data determined not to be proper has been acquired. In addition, the surrounding scanning lines may be a plurality of scanning lines provided before and after the scanning line on which the OCT data determined not to be proper has been acquired. For example, the surrounding scanning lines may be scanning lines provided at least any of before and after the scanning line on which the OCT data determined not to be proper has been acquired. The surrounding scanning lines may include at least a scanning line on which OCT data determined to be proper by the processor has been acquired or may include a scanning line on which OCT data determined not to be proper by the processor has been acquired. For example, in the example, interpolation of an alternative to OCT data determined not to be proper is performed by using OCT data acquired on such surrounding scanning lines, and thus it is possible to acquire a favorable imaged image of the subject eye with high efficiency.

For example, in the example, the processor interpolates the alternative to the OCT data determined not to be proper, based on OCT data determined to be proper by the processor, which is acquired in scanning on at least any one of scanning lines before and after the scanning line on which the OCT data determined not to be proper by the processor has been acquired. That is, in the example, only OCT data corresponding to a scanning line determined to be proper by the processor is used in interpolation processing. Therefore, even in a case where OCT data corresponding to the scanning line determined not to be proper by the processor is used in interpolation processing, it is possible to improve accuracy of interpolation processing.

The processor may interpolate an alternative to the OCT data determined not to be proper by performing copying processing of OCT data corresponding to the surrounding scanning lines of the scanning line on which OCT data determined not to be proper by the processor has been acquired or corresponding to at least any one of scanning lines before and after the scanning line on which the OCT data determined not to be proper by the processor has been acquired. The processor may interpolate an alternative to the OCT data determined not to be proper by performing interpolation processing on OCT data corresponding to the surrounding scanning lines of the scanning line on which OCT data determined not to be proper by the processor has been acquired or corresponding to at least any one of scanning lines before and after the scanning line on which the OCT data determined not to be proper by the processor has been acquired. As an example, a frame interpolation technique or a super resolution technique may be used for the interpolation processing. For example, the processor may have a configuration of performing both of the copying processing and the interpolation processing or have a configuration of performing at least one of the copying processing and the interpolation processing.

For example, in the example, such an processor may interpolate an alternative to motion contrast data determined not to be proper by the processor, based on motion contrast data around a scanning line on which the motion contrast data determined not to be proper has been acquired.

For example, in the example, the motion contrast data may be front face motion contrast data corresponding to the scanning line. The processor may interpolate an alternative to front face motion contrast data determined not to be proper by the processor, based on front face motion contrast data around a scanning line on which the front face motion contrast data determined not to be proper has been acquired. For example, in a case where front face motion contrast data obtained by integrating motion contrast data is obtained, and interpolation processing is performed on the obtained front face motion contrast data, it is possible to reduce the volume of data used in interpolation processing in comparison to a case where interpolation processing is performed on motion contrast data, and front face motion contrast data is obtained by integrating the resultant of the interpolation processing. Therefore, it is possible to acquire an imaged image of the subject eye with high efficiency.

<Detection of Movement of Subject Eye>

The processor traces and detects the movement of the subject eye. The processor may have a configuration of tracing the movement of the subject eye by detecting a feature region from front face image data acquired by the infrared imaging optical system. As an example, the processor may trace the movement of the subject eye by detecting a feature region from SLO data of the subject eye acquired with the SLO device in real time. The feature region of the subject eye may be detected from all frames in the acquired SLO data or detected at a predetermined frame interval (for example, a two frame interval) in the acquired SLO data. For example, thus, it is possible to normally detect the position-shifted amount of the subject eye.

<Tracking>

The processor controls the scanner based on the detection result of the movement of the subject eye to correct a scanning line for the subject eye. For example, the processor may control driving of the scanner 108 based on the position-shifted amount of the subject eye and correct the feature region in which the scanning line of the measurement light is detected. Thus, it is possible to properly scan with the measurement light even though the position of the subject eye is shifted.

For example, when the ophthalmic imaging apparatus has such a configuration, the processor may stop the control based on the detection result and change the scanning line for the measurement light to the next scanning line in a case where correction of the scanning line is not stably performed. Thus, for example, even in a case where the subject eye moves, and thus correction (that is, tracking) of the scanning line is not stably performed, the scanning line for the measurement light is changed to the next scanning line. OCT data on a scanning line of which correction is not stably performed is not acquired. However, if OCT data is acquired by performing interpolation on the above OCT data, it is possible to reduce imaging time of the subject eye and to acquire imaged image of the subject eye with high efficiency.

For example, the ophthalmic imaging apparatus may have a configuration of performing scanning with the measurement light after the scanning line is corrected by tracking. In this case, in a case where predetermined time elapses from a start of tracking, it may be determined that tracking is not stable. For example, the ophthalmic imaging apparatus may have a configuration of performing scanning with the measurement light while correcting the scanning line by tracking. In this case, when the shift of the position of the subject eye is detected by the SLO device, it may be determined that tracking is not stable. In this case, when plural OCT data acquired on one scanning line by the OCT optical system includes OCT data different from other OCT data, it may be determined that tracking is not stable. That is, it may be determined whether or not the position of the subject eye is shifted, based on the OCT data.

In a case where the position of the subject eye is largely shifted, the number of OCT data determined not to be proper is large with respect to the total number of acquired OCT data. Similarly, the number of scanning lines on which OCT data determined not to be proper has been acquired is large with respect to the total number of scanning lines on which scanning with the measurement light has been performed.

Therefore, the processor may determine whether or not tracking is stable, for example, from the accumulated value of OCT data determined not to be proper and the accumulated value of a scanning line on which OCT data determined not to be proper has been acquired.

The present disclosure is not limited to the apparatus described in the embodiment. For example, terminal control software (program) described below of performing functions in the embodiment may be supplied to a system or an apparatus via a network or various storage media, and a control device (for example, a CPU) of the system or the apparatus may read and execute the program.

EXAMPLE

A typical example in the present disclosure will be described below with reference to the drawings. FIG. 1A is a diagram illustrating an optical system and a control system of the ophthalmic imaging apparatus. Descriptions will be made on the assumption that an axial direction (forth-and-back direction) of the subject eye E is set as a Z-direction, a horizontal direction (right-and-left direction) is set as the X-direction, and a vertical direction (up-and-down direction) is set as the Y-direction. A surface direction of a fundus Ef of an subject eye E may be considered as the XY directions.

Figure 1B:
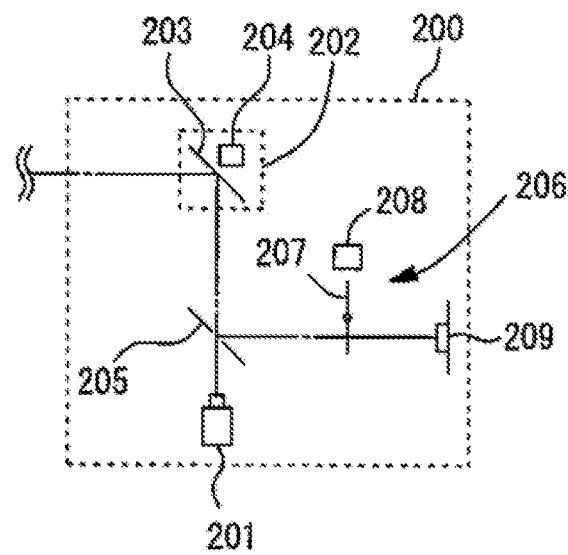
FIG. 1B is a diagram illustrating an observation optical system of the ophthalmic imaging apparatus.

In the example, the ophthalmic imaging apparatus 1 is an ophthalmic imaging apparatus obtained by combining an OCT device and an SLO device. In the example, the ophthalmic imaging apparatus 1 images the fundus Ef of the subject eye E. The ophthalmic imaging apparatus 1 may image an anterior segment (for example, a cornea and a crystalline lens) of the subject eye E. For example, the ophthalmic imaging apparatus 1 includes the OCT optical system 100, an observation optical system 200, a fixation guidance portion 300, and the control unit 70. FIG. 1B is a diagram illustrating the observation optical system 200 of the ophthalmic imaging apparatus 1.

<OCT Optical System>

The OCT optical system 100 has a configuration of a so-called optical coherence tomography (OCT). The OCT optical system 100 images the fundus Ef of the subject eye E so as to acquire OCT data thereof. The OCT optical system 100 may acquire an OCT signal obtained by processing an interference signal or acquire an image generated from the OCT signal, as the OCT data. The OCT optical system 100 may acquire a tomographic image, acquire a front face image created based on the tomographic image, or acquire a motion contrast image created based on arithmetic processing described later, as the OCT data. For example, in the example, a motion contrast (hereinafter, MC) image of the subject eye is acquired by the OCT optical system 100. For example, the MC image may be an image in which movement of the blood flow or the blood vessel region is represented by a luminance value based on the OCT data.

For example, the OCT optical system 100 may be time domain OCT (TD-OCT). For example, the OCT optical system 100 may be Fourier domain OCT (FD-OCT). As the FD-OCT, spectral domain OCT (SD-OCT) or swept source OCT (SS-OCT) is representative. In the example, a case where SD-OCT is applied to the OCT optical system 100 will be described.

For example, the OCT optical system 100 splits light emitted from a light source 102 into measurement light and reference light and acquires an interference signal between the measurement light with which the subject eye E is irradiated and the reference light. For example, the OCT optical system 100 includes the light source 102, a coupler (light splitter) 104, the scanner (for example, an optical scanner) 108, a measurement optical system 106, the detector 120, and a reference optical system 130. For example, the light source 102, the measurement optical system 106, the detector 120, and the reference optical system 130 are linked to the coupler 104 by optical fiber.

In the example, the OCT optical system 100 splits the light emitted from the light source 102 into the measurement light and the reference light by the coupler 104. The measurement light passes in optical fiber and then is emitted into an air. Then, the measurement light is guided to the fundus Ef through the scanning unit 108 and the measurement optical system 106. The reference light passes in optical fiber, and then is guided to the reference optical system 130. The measurement light reflected by the fundus Ef and the reference light reflected by a reflection optical system described later are brought back to the optical fiber via similar paths. The OCT optical system 100 causes the detector 120 to receive an interference signal (interference light) obtained by composition of the measurement light and the reference light.

For example, the light source 102 is a low-coherent light source (broadband light source) that emits low coherent light used as the measurement light and the reference light of the OCT optical system 100. For example, the light source 102 may be a light source that performs irradiation with light having a center wavelength in a range of $\lambda$=800 nm to 1100 nm. For example, the light source 102 may be a super luminescent diode (SLD) light source.

For example, the detector 120 detects an interference signal obtained by composition of the measurement light and the reference light. For example, the detector 120 has a spectroscopic optical system (spectrometer) that disperses the interference signal into wavelength components (frequency components). For example, the spectrometer includes a diffraction grating and a line sensor. The interference signal detected by the detector 120 is output to the control unit 70.

For example, the control unit 70 processes the interference signal so as to acquire an OCT signal. For example, the control unit 70 performs Fourier transform on the OCT signal so as to acquire a complex OCT signal. For example, the control unit 70 obtains a depth profile (A scan data) of the subject eye E in a predetermined range by calculating the absolute value of the amplitude of the complex OCT signal. That is, signal intensity in the depth direction of the subject eye E is acquired. For example, the control unit 70 arranges the depth profile in each scanning line for the measurement light with which the scanner 108 scans, so as to acquire tomographic image data (B scan data) of the subject eye E. Each piece of data may be signal data or may be image data generated from the signal data.

For example, the control unit 70 acquires an MC image from at least two or more complex OCT signals which are different from each other in time and relate to the same scanning line for the subject eye E. That is, the control unit acquires the MC image by performing analysis processing of at least two or more complex OCT signals. For example, the control unit 70 acquires a three-dimensional MC image by arranging MC images in each scanning line for the measurement light with which the scanner 108 scans, in a two-dimensional range relating to a direction orthogonal to the depth direction.

The scanner 108 scans on the fundus Ef with the measurement light in the XY directions (transverse direction). For example, the scanner 108 is disposed at a position which is substantially conjugate with the pupil of the subject eye E. For example, the scanner 108 includes two galvano mirrors, and the reflection angle thereof is randomly adjusted by a drive mechanism 50. Thus, a reflection (traveling) direction of the light emitted from the light source 102 changes, and thus an imaging position on the fundus Ef is changed. The scanner 108 may have a configuration of polarizing the light. For example, an acousto-optic module (AOM) that changes a traveling (deflection) direction of light may be used in addition to a reflective mirror (galvano mirror, polygon mirror, resonant scanner, and the like).

The reference optical system 130 generates the reference light to be composed with the measurement light reflected by the fundus Ef. The reference optical system 130 may be a Michelson type or a Mach-Zehnder type. For example, the reference optical system 130 is formed by a reflective optical system (for example, a reference mirror). The reference light from the coupler 104 to be reflected by the reflection optical system, is brought back to the coupler 104, and then is guided to the detector 120.

As another example, the reference optical system 130 is formed by a transmission optical system (for example, an optical fiber). The reference light from the coupler 104 may be guided to the detector 120 by being transmitted without being brought back to the coupler 104.

The reference optical system 130 has a configuration of changing an optical path length difference between the measurement light and the reference light by moving an optical member on a reference optical path. For example, the reference mirror is moved in an optical axis direction. A configuration of changing the optical path length difference may be disposed on a measurement optical path in the measurement optical system 106.

<Observation Optical System>

The observation optical system 200 has a configuration of a so-called scanning laser ophthalmoscope (SLO). The observation optical system images the fundus Ef of the subject eye E so as to acquire an SLO front face image thereof. The observation optical system 200 may have a configuration of a so-called fundus camera type. The observation optical system 200 may be an infrared imaging optical system that images a subject eye with an infrared ray.

For example, the observation optical system 200 includes a laser light source 201, a scanner 204, a perforated mirror 205, a rotating plate portion 206, and a light receiving element 209. The observation optical system 200 may appropriately include other optical elements. For example, the laser light source 201 may emit at least laser light having a first wavelength (for example, a wavelength in the vicinity of a wavelength of 790 nm) and laser light having a second wavelength (for example, a wavelength in the vicinity of a wavelength of 490 nm). The laser light source 201 may emit only monochromatic light.

For example, laser light from the laser light source 201 passes through an opening portion of the perforated mirror 205 in which the opening portion is provided at the center, and then is directed toward the scanner 204. Laser light reflected by the scanner 204 passes through the measurement optical system 106, and then is condensed at the fundus Ef. Light is emitted from the fundus Ef with irradiating the fundus Ef with the laser light from the laser light source 201. For example, the laser light is scattered and reflected by the fundus Ef. As a result, light (hereinafter, fundus-reflected light) which is scattered and reflected by the fundus Ef is emitted through the pupil. The laser light may cause fluorescent substances at the fundus Ef to be excited. Therefore, fluorescent light emitted from the fluorescent substances at the fundus Ef may be emitted through the pupil.

The scanner 204 scans on the fundus Ef with the laser light guided from the laser light source 201 and changes the traveling direction of the laser light (in other words, deflects the laser light). In the example, the scanner 204 includes a reflective mirror 203. For example, the reflective mirror 203 may be a galvano mirror and a polygon mirror. A resonant scanner, an acousto-optic module (AOM), or the like may be used as the scanner 204.

The rotating plate portion 206 selects the wavelength of light received by the light receiving element 209. The rotating plate portion 206 includes a rotating plate 207, a driving portion 208, and the like. For example, the rotating plate 207 includes a plurality of barrier filters for observing the fluorescence generated in the fundus Ef. For example, the rotating plate 207 is rotated by the driving portion 208, and thereby various barrier filters are set on an optical path toward the light receiving element 209.

For example, a barrier filter for infrared fluorescence imaging and a barrier filter for visible fluorescence imaging are provided in the rotating plate 207. For example, the barrier filter for infrared fluorescence imaging may be used as a barrier filter for indocyanine green angiography (ICGA) imaging which is one of infrared fluorescence imaging. ICGA imaging is fluorescence imaging using indocyanine green as a fluorescence fundus contrast agent. For example, in a case of performing ICGA imaging, irradiation with laser light having a first wavelength is performed from the laser light source 201, and fluorescence in the vicinity of a wavelength which is 800 nm to 860 nm is imaged through the barrier filter for infrared fluorescence imaging. ICGA imaging is mainly used for observing a choroidal blood vessel.

For example, the barrier filter for visible fluorescence imaging may be used as a barrier filter for fluorescein-angiography (FA) imaging. FA imaging is fluorescence imaging using fluorescein as a fluorescence fundus contrast agent. For example, in a case of performing FA imaging, irradiation with laser light having a second wavelength is performed, and fluorescence in the vicinity of a wavelength which is 510 nm to 550 nm is imaged through the barrier filter for visible fluorescence imaging. FA imaging is mainly used for observing a retinal blood vessel.

The light receiving element 209 receives light (that is, fundus-reflected light in normal imaging and fluorescence generated in the fundus Ef in fluorescent imaging) from the fundus Ef along with the laser light with which irradiation is performed from the laser light source 201. For example, in fluorescent imaging, the control unit 70 acquires an SLO fluorescent front face image of the fundus Ef based on a light reception signal from the light receiving element 209.

In a case where the fundus Ef is irradiated with the laser light, light which is reflected or emitted by the fundus Ef passes through the measurement optical system 106 and the scanner 204 and is reflected by the perforated mirror 205. Then, the light is guided to the light receiving element 209 through the filter of the rotating plate 207. The position of the pupil of the subject eye E and the opening portion of the perforated mirror 205 may have an optically conjugate relationship.

<Fixation Guidance Portion>

The fixation guidance portion 300 includes an optical system that guides a sight line direction of the subject eye E. The fixation guidance portion 300 includes a fixation lamp to be presented to the subject eye E and two-dimensionally changes the presentation position of the fixation lamp. As a result, the line of sight of the subject eye E is guided in a plurality of directions, and thus, the imaging region is changed. For example, if the fixation lamp is presented in the same direction as an imaging optical axis, the central portion of the fundus Ef is set as the imaging region. For example, if the fixation lamp is presented upward with respect to the imaging optical axis, the upper portion of the fundus Ef is set as the imaging region. That is, the imaging region of the subject eye E is changed in accordance with the position of the fixation lamp with respect to the imaging optical axis.

For example, for the fixation guidance portion 300, a configuration in which the fixation position of the subject eye E is adjusted by changing a lighting position of the fixation lamp (for example, a light emitting diode (LED)) arranged in a matrix, a configuration in which the fixation position of the subject eye E is adjusted in a manner that scanning with light from the light source is performed with an optical scanner, and lighting of the light source is controlled, and the like are considered. The fixation guidance portion 300 may be an internal fixation light type or an external fixation light type.

<Control Unit>

The control unit 70 is generally implemented by a CPU (processor) 71, a ROM 72, a RAM 73, and the like. For example, the CPU 71 controls driving of each portion in the ophthalmic imaging apparatus 1. For example, various programs executed by the CPU 71 are stored in the ROM 72. For example, the RAM 73 temporarily stores various kinds of information. The control unit 70 may be constituted by a plurality of processors.

For example, the control unit 70 is electrically connected to a storage portion (for example, a non-volatile memory) 74, a display portion (for example, a monitor) 75, and an operation portion 76. For example, the control unit 70 controls a display screen of the monitor 75. The monitor 75 displays SLO front face data by the observation optical system 200, OCT data by the OCT optical system 100, and the like. For example, the monitor 75 may be a monitor (display) mounted in the main body of the ophthalmic imaging apparatus 1, or may be a monitor connected to the main body of the ophthalmic imaging apparatus 1. For example, a monitor of a personal computer may be used as the monitor 75. Combination of a plurality of monitors may be used as the monitor 75. The monitor 75 may be a touch panel. In such a case, the monitor 75 functions as the operation portion 76.

Various operation instructions by the examiner are input to the operation portion 76. The operation portion 76 outputs a signal corresponding to the input operation instruction to the control unit 70. For example, at least one of user interfaces such as a mouse, a joystick, a keyboard, and a touch panel may be used as the operation portion 76. The control unit 70 may acquire an operation signal based on an operation of the examiner, which is by the operation portion 76.

The non-volatile memory 74 (hereinafter, memory 74) may be a non-transitory storage medium capable of retaining stored contents even though the supply of power is cut off. For example, a hard disk drive, a flash ROM, and a removable USB memory can be used as the memory 74. The memory 74 may store information (for example, an imaging position in the fundus Ef) regarding imaging of the acquired OCT data, in addition to the acquired OCT data.

For example, the control unit 70 controls the fixation guidance portion 300 to change the representation position of the fixation lamp. For example, the control unit 70 acquires the interference signal output from the detector 120 provided in the OCT optical system 100 and a light reception signal output from the light receiving element provided in the observation optical system 200. For example, the control unit 70 controls the scanner 108 to changes an irradiation position of the measurement light for the subject eye E. For example, the control unit 70 controls the scanner 108 to change an irradiation position of the laser light for the subject eye E.

<Control Operation>

A control operation in which the ophthalmic imaging apparatus 1 images the fundus Ef of the subject eye E so as to acquire an MC image will be described below as an example.

<Alignment of Subject Eye>

Firstly, the examiner performs alignment between the subject eye E and the ophthalmic imaging apparatus 1. The control unit 70 lights the fixation lamp provided in the fixation guidance portion 300. The control unit 70 lights a light source provided in a target projection system (not illustrated). Thus, an alignment index image is projected onto the subject eye E. The anterior segment of the subject eye E is detected by a camera (not illustrated) for anterior segment observation. An anterior segment observation image is displayed in the monitor 75. The examiner instructs a subject to gaze at the fixation lamp. Then, the examiner operates the operation portion 76 (for example, a joystick (not illustrated)) while looking at the anterior segment observation image and the alignment index image so as to perform alignment for matching the corneal apex position (or the approximate corneal apex position) of the subject eye E with a measurement optical axis. A configuration in which the control unit 70 detects position shift between the corneal apex position and the measurement optical axis by using the alignment index image, and such alignment is automatically performed may be made.

<Acquisition of SLO Front Face Image>

If alignment is finished, the examiner images the fundus Ef with the observation optical system 200 so as to acquire an SLO front face image. The control unit 70 controls the optical scanner provided in the observation optical system 200 to scan on the fundus Ef with the laser light having the first wavelength, with which irradiation is performed from the laser light source 201. The control unit 70 acquires the light reception signal transmitted from the light receiving element 209, as the SLO front face image of the fundus Ef. The SLO front face image is displayed in the monitor 75 and is stored in the memory 74 as a reference image of determination processing described later.

<Setting of Scanning Line>

Figure 3A:
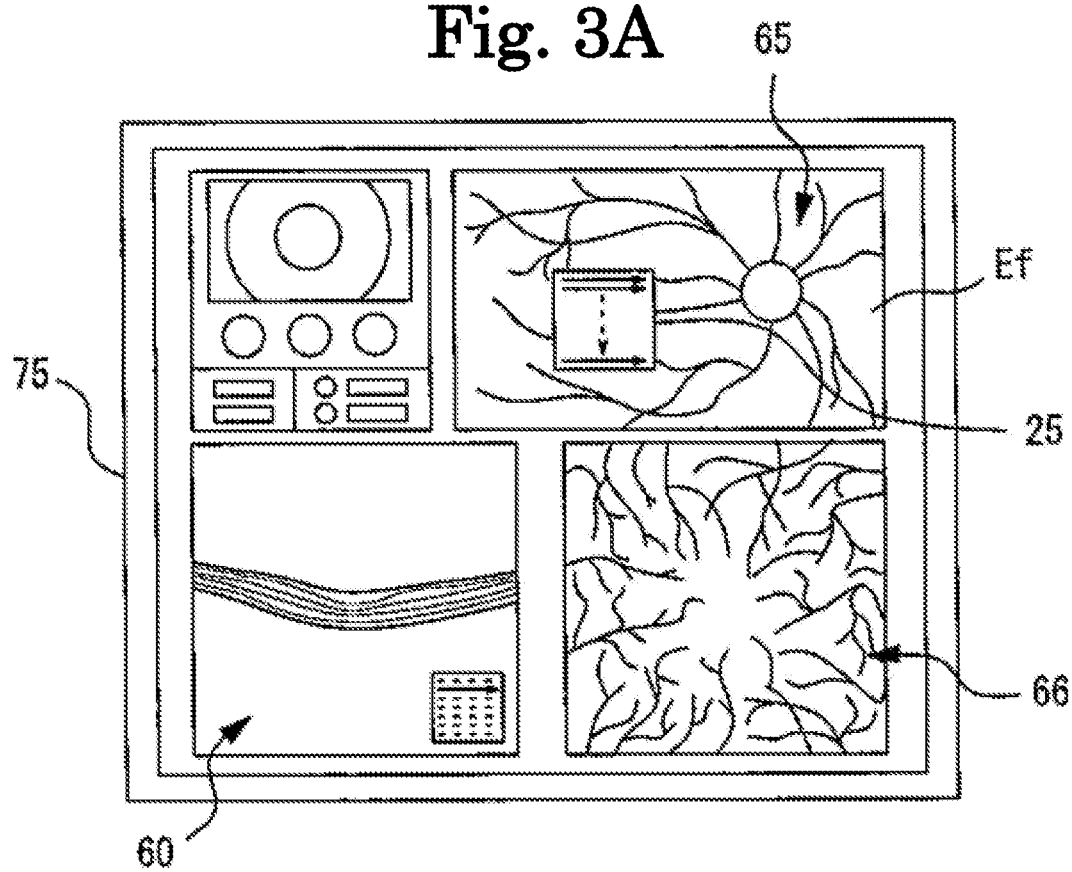
FIGS. 3A and 3B illustrate examples of a display screen of a monitor.
Figure 3B:
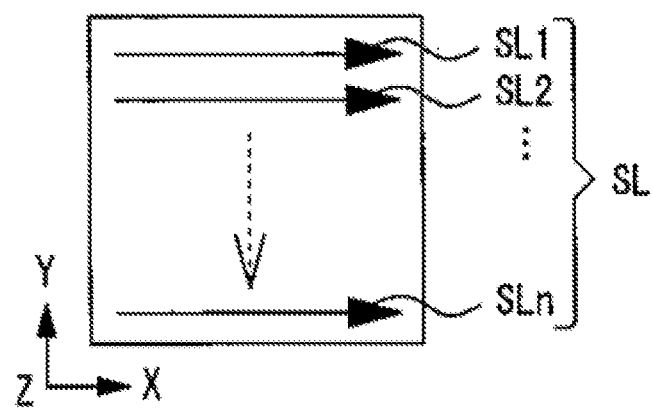

The examiner sets a scanning line of the measurement light for the subject eye E by using the acquired SLO front face image. FIGS. 3A and 3B illustrate examples of a display screen of the monitor 75. FIG. 3A illustrates the entirety of the monitor 75. FIG. 3B is a diagram of enlarging an index 25 displayed in the monitor 75. For example, the index 25 and the acquired SLO front face image 65 are displayed in the monitor 75. For example, a front face MC image 66 described later and a tomographic image 60 at a specific position of the front face MC image 66 may be displayed in the monitor 75.

The index 25 is an index indicating an imaging position of the front face MC image 66 and a scanning pattern of the measurement light. For example, the index 25 is electrically superimposed and displayed on the SLO front face image 65. The display form of the index 25 is changed based on the set scanning pattern (for example, a line scan, a raster scan, a circle scan, and a radial scan).

For example, the examiner operates the operation portion 76 (for example, a drag operation) so as to move the index 25 on the SLO front face image 65. Thus, a scanning line for scanning on the fundus Ef with the measurement light in the OCT optical system 100 is set. That is, the position at which the fundus Ef is imaged is set by the examiner moving the position of the index 25.

For example, the control unit 70 images the fundus Ef so as to acquire an interference signal corresponding to a scanning line and performs determination processing on OCT data obtained by processing the interference signal, in accordance with the flowchart illustrated in FIG. 2. In the example, determination processing is performed on the OCT signal obtained by processing the interference signal.

<Acquisition of OCT Signal and SLO Front Face Image>

The examiner images the fundus Ef with the OCT optical system 100. If a signal for starting imaging is input, the control unit 70 drives the scanner 108 based on a display position of the index 25 to scan with the measurement light so as to obtain an OCT signal of the fundus Ef corresponding to the position of the index 25. A relationship between the display position (coordinate position on the monitor 75) of the index 25 and the scanning line for the measurement light by the scanner 108 is preset. The control unit 70 controls driving of two galvano mirrors in the scanner 108 so as to scan with the measurement light in a scan range corresponding to the display position of the index 25. The control unit 70 acquires an OCT signal by scanning with the measurement light and controls the observation optical system 200 to acquire an SLO front face image. That is, the control unit 70 acquires the OCT signal by the OCT optical system 100 and acquires the SLO front face image by the observation optical system 200 together (S1).

For example, the control unit 70 acquires the OCT signal based on the set scanning lines (for example, scanning lines SL). For example, in the example, scanning lines on the fundus Ef are set in order of a first scanning line SL1, a second scanning line SL2, . . . , and the final scanning line SLn by the control unit 70. OCT signals are acquired based on the scanning lines by the detector 120. Here, a case of acquiring an OCT signal for the first scanning line SL1 is described as an example.

As illustrated in FIG. 3B, the control unit 70 controls the scanner 108 to scan with the measurement light along the first scanning line SL1 in the X-direction. Scanning with the measurement light in any direction (for example, X-direction) of the surface direction (XY-directions) of the fundus Ef is referred to as "B scanning". In the following descriptions, one OCT signal acquired by one B scanning is set to be an OCT signal of one frame. For example, in the example, the front face MC image 66 is acquired by arithmetically processing the acquired OCT signal (details will be described later). Thus, the control unit 70 controls the scanner 108 to scan on the same scanning line with the measurement light plural number of times and thus acquires OCT signal of a plurality of frames, which are different from each other in time with respect to the same scanning line. In this case, OCT signals of at least two frames may be acquired. In the example, OCT signals of four frames different from each other in time are acquired. For example, if first scanning on the first scanning line SL1 is finished, the control unit 70 performs second, third, and fourth scanning by scanning with the measurement light, so as to acquire OCT signals of four frames. That is, the control unit 70 acquires the OCT signals of the four frames for each one scanning line.

For example, the control unit 70 acquires an SLO front face image during a period in which scanning with the measurement light is performed four times, and thus the OCT signals of the four frames are acquired. For example, in the example, a frame rate when the SLO front face image is obtained is ¼ of a frame rate when the OCT signal is obtained. That is, OCT signals of four frames can be acquired in a period in which an SLO front face image of one frame is acquired.

<Determination of Whether or Not OCT Signal Is Proper>

If the OCT signals of the four frames on the first scanning line SL1 are acquired, the control unit 70 determines whether or not the acquired OCT signals are proper. For example, determination of whether or not the OCT signal is proper is performed in real time. For example, in the example, the control unit 70 detects the movement of the subject eye E by using an SLO front face image of one frame, which is acquired to correspond to OCT signals of four frames and an SLO front face image as a reference, which has been stored in the memory 74 (that is, the above-described reference image). The control unit 70 determines whether or not the OCT signal is proper, from the movement of the subject eye E.

The control unit 70 performs image processing on the two SLO front face images and detects a feature region of the subject eye. Image processing may be processing of extracting a specific region relating to a change in luminance, a shape, a size, and the like of the feature region.

For example, in the example, an optic disc of the subject eye is detected from edge detection on the two SLO front face images. The control unit 70 detects the position-shifted amount of the subject eye E from the position of the optic disc in the two SLO front face images (S2). A macula of the subject eye may be detected as the feature region of the subject eye, and the position-shifted amount of the subject eye E may be detected from the position of the macula. The position-shifted amount of the subject eye E may be detected by detecting the maximum value of correlation between the two SLO front face images or the minimum value of the error.

An allowable range may be provided in advance, for the position-shifted amount. The control unit 70 determines whether the position-shifted amount is within the allowable range (for example, within a predetermined threshold) (S3). In a case where the position-shifted amount is out of the allowable range, the control unit 70 determines that the OCT signal acquired on the first scanning line SL1 is not proper. The OCT signal determined not to be proper is not necessarily required in the front face MC image 66 described later. Thus, the control unit 70 deletes the OCT signal determined not to be proper (S4). The control unit 70 may also store the OCT signal determined not to be proper, in the memory 74 in association with the scanning line even though the OCT signal determined not to be proper is provided.

For example, in a case where the position-shifted amount is within the allowable range, the control unit 70 determines that the OCT signal acquired on the first scanning line SL1 is proper. The control unit 70 stores the OCT signal determined to be proper, in the memory 74 in association with the scanning line (S5).

<Determination of Number of Scanning Lines on which Improper OCT Signal Has Been Acquired>

Here, in the example, interpolation processing described later is performed for the front face MC image 66 based on the OCT signal determined not to be proper. If the improper OCT signals are consecutively acquired, this influences accuracy of interpolation processing. Thus, the number of scanning lines on which improper OCT signals are consecutively acquired is set to be equal to or less than a predetermined number of scanning lines. The predetermined number of consecutive scanning lines may have any value. In order to maintain accuracy of interpolation processing, the predetermined number of consecutive scanning lines is preferably set to be equal to or less than two which is the number of consecutive scanning lines. Regarding this, a case where it is determined that the OCT signal acquired on the fourth scanning line SL4 is not proper will be described as an example. In the example, when OCT signals determined not to be proper have been acquired on consecutive three scanning lines, the following control is performed, and thus the OCT signal determined not to be proper can be acquired on two consecutive scanning lines.

For example, the control unit 70 determines whether or not scanning lines on which an OCT signal determined not to be proper has been acquired are consecutive by a predetermined number of scanning lines (S6). For example, the predetermined number of scanning lines may be set in advance by experiments, simulations, or the like, or may be randomly set by the examiner. The number of scanning lines may be automatically changed in accordance with an imaging situation of the subject eye E. In the example, the predetermined number of scanning lines is set to be 3.

For example, in a case where it is determined that the OCT signal acquire don the fourth scanning line SL4 is determined not to be proper, the control unit 70 determines whether or not OCT signals determined not to be proper are acquired on consecutive three scanning lines. For example, the control unit 70 checks whether OCT signals on the second scanning line SL2 and the third scanning line SL3, which are stored in the memory 74 are proper.

For example, in a case where it is determined that the OCT signals on both the second scanning line SL2 and the third scanning line SL3 are not proper, the control unit 70 determines that the OCT signals determined not to be proper are acquired on consecutive three scanning lines. That is, it is determined that the OCT signals determined not to be proper have been consecutively acquired by the predetermined number of scanning lines. At this time, the control unit 70 controls the scanner 108 to scan with the measurement light on the fourth scanning line SL4 again (S7). For example, in the example, scanning on the fourth scanning line SL4 repeats until the OCT signal acquired on the fourth scanning line SL4 is determined to be proper. Thus, it is possible to reduce the number of corresponding scanning lines to two scanning lines or less even though OCT signals determined not to be proper are consecutive.

For example, in a case where it is determined that the OCT signal of at least one of the second scanning line SL2 and the third scanning line SL3 is determined to be proper, the control unit 70 determines that the OCT signals determined not to be proper are not acquired on consecutive three scanning lines. That is, it is determined that the OCT signals determined not to be proper are not consecutively acquired by the predetermined number.

<Determination of Finishing Imaging on All Scanning Lines>

The control unit 70 determines whether or not acquiring of OCT signals on all set scanning lines is finished. That is, the control unit 70 determines whether or not imaging up to the final scanning line SLn is finished (S8). For example, in a case where it is determined that the OCT signal on the final scanning line SLn is not acquired, the control unit 70 controls driving of the scanner 108 to change the scanning line to the next scanning line (S9). On the changed scanning line, an OCT signal and an SLO front face image are acquired, it is determined whether or not the OCT signal is proper, and it is determined whether or not the scanning line is the final scanning line SLn. For example, in a case where it is determined that the OCT signal on the final scanning line SLn has been acquired, the control unit 70 ends imaging of the subject eye E (S10).

<Acquisition of Motion Contrast Image>

For example, the control unit 70 performs Fourier transform on the OCT signal acquired on each scanning line SL so as to acquire a complex OCT signal including a real component and an imaginary component. For example, the control unit 70 acquires an MC image by performing processing relating to the Doppler phase difference method and processing related to a vector difference method on the complex OCT signal. As a method of processing the complex OCT signal, a method of calculating a phase difference of the complex OCT signal, a method of calculating a vector difference of the complex OCT signal, a method of multiplying the phase difference and vector difference of the complex OCT signal, and the like are considered. In the example, the method of multiplying the phase difference and vector difference is described.

For example, the control unit 70 calculates a phase difference between complex OCT signals obtained by transforming OCT signals which have been acquired on the same scanning line and are different from each other in time. For example, the control unit 70 removes a random phase difference provided in a region in which a S/N ratio (signal-to-noise ratio) is low. For example, the control unit 70 removes a portion with a small phase difference in order to remove a reflection signal from a highly reflective portion such as an NFL (neural fiber layer). Thus, it is easy to determine whether the signal is a signal from the highly reflective portion or a signal from a blood vessel. For example, in the example, one frame in which the phase difference is calculated is acquired. In a case where a plurality of frames for calculating the phase difference is provided, signals of the frames, which are subjected to the above processing may be subjected to addition averaging processing and remove noise.

Then, the control unit 70 calculates a vector difference of the complex OCT signal. For example, the complex OCT signal can be represented by a vector on a complex plane. The control unit 70 detects two signals which have been acquired on the same scanning line and are different from each other in time and calculates a vector difference between the signals, and thus it is possible to generate a contrast image in the subject eye. In a case where the vector difference is expressed as an image, the imaging may be performed based on phase information in addition to the magnitude of the difference. For example, in the example, one frame for calculating the vector difference is acquired. In a case where a plurality of frames for calculating the vector difference is provided, signals of the frames, which are subjected to the above processing may be subjected to addition averaging processing and remove noise.

For example, the control unit 70 uses a calculation result of the phase difference as a filter, for a calculation result of the vector difference. In the example, "filtering" means weighting a certain numerical value. For example, the control unit 70 performs weighting by applying the calculation result of the phase difference to the calculation result of the vector difference. That is, the calculation result of the vector difference is weighted by the calculation result of the phase difference. Thus, the vector difference at a portion of a small phase difference is small, and the vector difference at a portion of a large phase difference is large. For example, in the example, as described above, the calculation result of the vector difference and the calculation result of the phase difference are multiplied, and thereby the MC image weighted by the calculation result of the phase difference is generated. The control unit 70 performs the arithmetic processing on each scanning line so as to acquire an MC image of each scanning line.

The arithmetic processing may be performed in parallel while OCT signals of four frames are acquired in each scanning line by scanning of the measurement light. The processing may be performed after the OCT signals of the four frames on all scanning lines. With such arithmetic processing, an MC image of the subject eye E is acquired. For example, the MC image may be an front face MC image relating to a predetermined region (for example, a specific layer, a region at a predetermine depth) in the depth direction constructed based on the MC image acquired on each scanning line.

<Interpolation of Front Face Motion Contrast Image>

Figure 4:
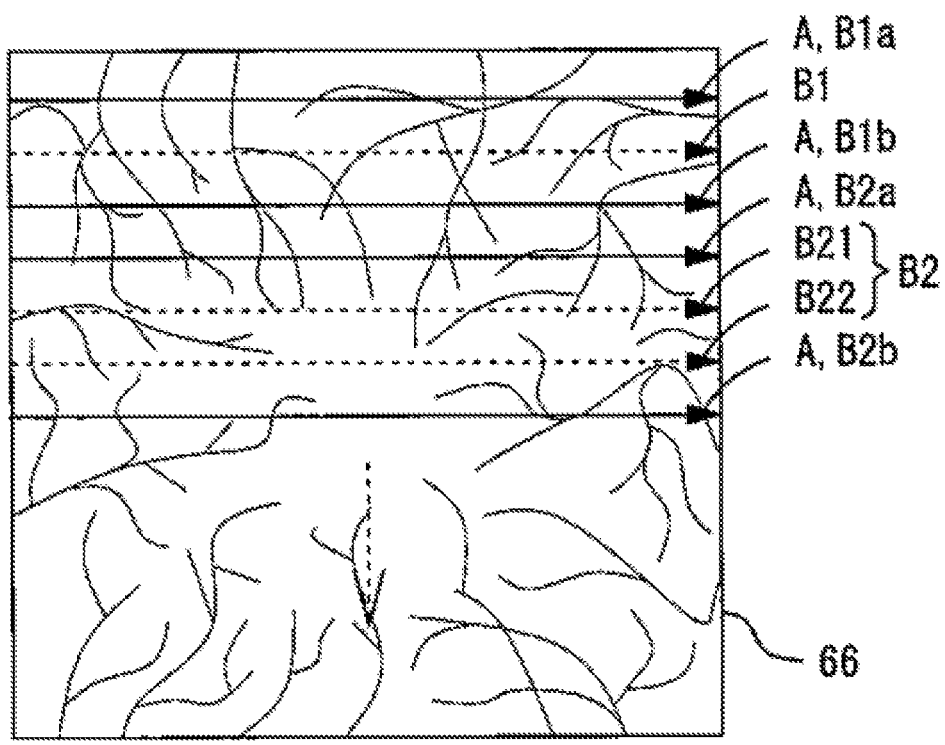
FIG. 4 illustrates an example of a front face motion contrast image.

FIG. 4 illustrates an example of the acquired front face MC image 66. For example, in the front face MC image in FIG. 4, a scanning line (scanning line indicated by a solid line) on which the OCT signal determined to be proper by the control unit 70 has been acquired is set as a scanning line A. Scanning lines (scanning lines indicated by dot lines) on which the OCT signal determined not to be proper by the control unit 70 has been acquired are set as scanning lines B1 and B2. For example, in the example, only the OCT signal determined to be proper is stored in the memory 74, and a front face MC image corresponding to the OCT signal is acquired. Therefore, the front face MC image corresponding to the OCT signal determined not to be proper is not acquired, and thus, the front face MC image 66 is in a state where a portion of the front face MC image 66 is missed.

For example, the control unit 70 interpolates an alternative to the front face MC image (that is, front face MC images corresponding to the scanning lines B1 and B2) corresponding to the scanning line on which the OCT signal determined not to be proper has been acquired, based on front face MC images corresponding to the surrounding scanning lines of the scanning line on which the OCT signal determined not to be proper has been acquired. In the example, a front face MC image corresponding to at least any scanning line of before and after the scanning line on which the OCT signal determined not to be proper has been acquired is used in interpolation processing. For example, interpolation processing may be copying processing of copying a front face MC image corresponding to at least any scanning line of before and after the scanning line on which the OCT signal determined not to be proper has been acquired. The interpolation processing may be interpolation processing of interpolating the front face MC image corresponding to at least any scanning line of before and after the scanning line on which the OCT signal determined not to be proper has been acquired. As the interpolation processing, a frame interpolation technology may be used. Super resolution processing (for example, interpolation processing such as a bilinear method, a nearest neighbor method, and a bicubic method) using a super resolution technology of outputting an image having a high resolution from one or a plurality of images may be performed.

For example, the scanning line B1 corresponding to one scanning line on which the OCT signal determined not to be proper by the control unit 70 has been acquired, and the scanning line B2 corresponding to a plurality of consecutive scanning lines on which the OCT signal determined not to be proper by the control unit 70 has been acquired are provided in the front face MC image 66. In the example, the scanning line B2 corresponds to two consecutive scanning lines and is constituted by a first scanning line B21 and a second scanning line B22.

In the example, the control unit 70 applies interpolation processing to the front face MC image corresponding to the scanning line B1. For example, the control unit 70 performs interpolation processing on the front face MC image of the scanning line B1 by using the front face MC image corresponding to a scanning line B1a before the scanning line B1 and the MC image corresponding to a scanning line B1b after the scanning line B1. Thereby, the front face MC image of the scanning line B1 on which the OCT signal determined not to be proper by the control unit 70 has been acquired is acquired.

In the example, the control unit 70 applies copying processing to the front face MC image corresponding to the scanning line B2. For example, the control unit 70 performs copying processing on the front face MC image corresponding to a scanning line B2a before the scanning line B21, and performs copying processing on the front face MC image corresponding to a scanning line B2b after the scanning line B22. Thereby, the front face MC image of the scanning line B2 on which the OCT signal determined not to be proper by the control unit 70 has been acquired is acquired.

For example, thus, the control unit 70 can compose the front face MC image (that is, front face MC image of the scanning line A) corresponding to the OCT signal determined to be proper and the front face MC image acquired by interpolation processing, and acquire the front face MC image 66 subjected to interpolation. At least one of interpolation processing and copying processing may be applied to the front face MC images corresponding to the scanning lines B1 and B2. This is not limited to the example.

As described above, for example, in the example, the ophthalmic imaging apparatus includes the scanner that scans with measurement light on a scanning line on the subject eye, the processor that determines whether or not the OCT data acquired on the scanning line is proper, the processor that controls the scanner based on the determination result of the processor to change the scanning line for the measurement light to the next scanning line, and the processor that interpolates an alternative to OCT data determined not to be proper by the processor, based on OCT data corresponding to scanning lines around a scanning line on which the OCT data determined not to be proper has been acquired. The scanning line for the measurement light is changed regardless of whether or not OCT data acquired on each scanning line is proper, in accordance with the determination result of the processor. Thus, it is possible to reduce imaging time of the subject eye and to reduce a burden on a subject. Since the OCT data determined not to be proper is subjected to interpolation, it is possible to acquire a favorable imaged image of a subject eye with high efficiency.

For example, in the example, in a case where OCT data determined not to be proper are consecutively acquired in scanning of the predetermined number of scanning lines, the ophthalmic imaging apparatus causes the scanner to continue to scan with the measurement light on the same scanning line until the OCT data determined to be proper by the processor is acquired. Therefore, the situation in which OCT data which are determined not to be proper and correspond to the predetermined number or more of scanning lines are consecutively acquired does not occur.

Accordingly, it is possible to secure OCT data constructed by the interpolation processing, with uniform accuracy.

For example, in the example, the ophthalmic imaging apparatus interpolates an alternative to the OCT data determined not to be proper by the processor, based on OCT data determined to be proper by the processor, which is acquired in scanning on at least any one of scanning lines before and after the scanning line on which the OCT data determined not to be proper has been acquired. Since only OCT data determined to be proper before and after is used in interpolation processing, it is possible to improve accuracy of interpolation processing.

For example, in the example, in the ophthalmic imaging apparatus, the OCT data is the motion contrast data acquired by arithmetically processing the interference signal. The processor interpolates an alternative to the motion contrast data determined not to be proper, based on motion contrast data of scanning lines around the scanning line on which the motion contrast data determined not to be proper has been acquired. For example, the motion contrast data has a need to obtain at least two or more OCT signals on one scanning line, and thus it is easy to extend the imaging time of the subject eye. With the present disclosure, even in a case of acquiring the motion contrast data, it is possible to reduce the imaging time and to reduce the burden on a subject. In addition, it is possible to acquire the imaged image of the subject eye with high efficiency.

For example, in the example, in the ophthalmic imaging apparatus, the motion contrast data is front face motion contrast data corresponding to the scanning line. The processor interpolates an alternative to the front face motion contrast data determined not to be proper, based on front face motion contrast data of scanning lines around the scanning line on which the front face motion contrast data determined not to be proper has been acquired. For example, in a case where front face motion contrast data obtained by integrating motion contrast data is obtained, and interpolation processing is performed on the obtained front face motion contrast data, it is possible to reduce the volume of data used in interpolation processing in comparison to a case where interpolation processing is performed on motion contrast data, and front face motion contrast data is obtained by integrating the resultant of the interpolation processing. Therefore, it is possible to acquire an imaged image of the subject eye with high efficiency.

Modification Examples

In the example, a configuration in which the three-dimensional MC image is acquired by arranging MC images in each scanning line for the measurement light in the two-dimensional range relating to the direction orthogonal to the depth direction, and the front face MC image is subjected to interpolation is described as an example. However, it is not limited thereto. For example, the tomographic image (for example, the tomographic image 60 at the specific position of the MC image) in the front face MC image may be subjected to interpolation. For example, in this case, the control unit 70 may have a configuration of performing interpolation on the tomographic image corresponding to the OCT signal determined not to be proper, by using the tomographic image (B scan image) corresponding to the OCT signal in which the position-shifted amount of the subject eye E is within the allowable range and which is determined to be proper. In this case, the control unit 70 may construct the front face MC image in a state of performing interpolation on the tomographic image.

In the example, a configuration of detecting the movement of the subject eye E by using the SLO front face image acquired to correspond to the OCT signal and an SLO front face image (reference image) as a reference, which has been stored in the memory 74 is described as an example. However, it is not limited thereto. For example, the movement of the subject eye E may be detected by comparing an SLO front face image corresponding to an OCT signal of a scanning line on which scanning is performed with the measurement light and an SLO front face image corresponding to an OCT signal of a scanning line before one scanning line from the scanning line on which scanning is performed with the measurement light. As an example, the control unit 70 may detect the movement of the subject eye E by comparing an SLO front face image acquired to correspond to an OCT signal on the second scanning line SL2 to an SLO front face image acquired to correspond to an OCT signal on the first scanning line SL1.

In the example, a configuration of determining whether or not the OCT signal is proper, by using the SLO front face image is described as an example. However, it is not limited thereto. For example, it may be determined whether or not the OCT signal is proper, by using an anterior segment observation image detected by the camera (not illustrated) for anterior segment observation. In this case, a configuration in which image processing is performed on the anterior segment observation image so as to detect a corneal apex position of the subject eye E, and the position-shifted amount of the subject eye E is detected from the corneal apex position may be made. Thus, similar to a case using the SLO front face image, it is possible to determine whether or not the OCT signal is proper, from the movement of the subject eye E. Blink of the subject eye E may be detected by using the anterior segment observation image detected by the camera for anterior segment observation, and it may be determined whether or not the OCT signal is proper, from whether or not blink of the subject eye occurs.

For example, it may be determined whether or not the OCT signal is proper, by using the OCT signals of the four frames, which are acquired by the OCT optical system 100. In this case, when the OCT signal of at least one frame among the OCT signal of the four frames shows a waveform different from waveforms of the OCT signals of other frames, it may be determined that the OCT signal is not proper. In a case where intensity of the OCT signal is equal to or smaller than a predetermined threshold, it may be determined that the OCT signal is not proper.

In the above descriptions, determination of whether or not to be proper, by using the OCT signals of the four frames is described. However, whether or not to be proper may be determined by using the OCT signal of one frame. In this case, whether or not to be proper may be determined by comparing the OCT signal of one frame, which has been acquired on a scanning line to the OCT signal of one frame, which has been acquired on at least any of the previous scanning line and the subsequent scanning line.

In the example, a configuration of acquiring the OCT signals of four frames in a period in which the SLO front face image of one frame is acquired is described as an example. However, it is not limited thereto. For example, in the example, OCT signals of at least two frames may be acquired in the period in which the SLO front face image of one frame is acquired. The frame rate when the OCT signal is obtained and the frame rate when the SLO front face image is obtained may be respectively set such that OCT signals corresponding to the number of frames preset for acquiring the MC image.

In the example, a configuration of performing scanning four times (hereinafter, set as one set scanning) on each one scanning line is described as an example. However, it is not limited thereto. For example, scanning may be performed on one scanning line to correspond to a predetermined number of sets. In this case, the control unit 70 may control the scanner 108 to scan on the same scanning line with the measurement light a predetermined number of times (predetermined number of sets) and may change the scanning line of the measurement light to the next scanning line when the OCT signal determined to be proper is acquired until scanning corresponding to the predetermined number of sets is finished. In this case, the control unit 70 may control the scanner 108 to scan on the same scanning line with the measurement light a predetermined number of times (predetermined number of sets). In a case where the OCT signal determined not to be proper is acquired in scanning all the predetermined number of sets, the control unit 70 may change the scanning line of the measurement light to the next scanning line.

For example, as described above, in the example, the ophthalmic imaging apparatus controls the scanner to perform scanning on the same scanning line with the measurement light a predetermined number of times. In a case where the OCT data determined to be proper by the processor has been acquired and in a case where the OCT data determined not to be proper by the processor has been acquired in scanning of all the predetermined number of times, the processor changes the scanning line to the next scanning line. Thus, it is possible to reduce the number of scanning lines on which OCT data determined not to be proper is acquired, and the examiner can acquire a more favorable imaged image of the subject eye.

In the example, a configuration in which, when the OCT signal determined not to be proper is acquired on consecutive three scanning lines, scanning with the measurement light on the third scanning line is performed again, and thus the number of consecutive scanning lines on which the OCT signal determined not to be proper has been acquired is reduced up to two scanning lines or less is described. However, it is not limited thereto. For example, when the OCT signal determined not to be proper is acquired on consecutive three scanning lines, scanning with the measurement light may be performed again on at least any of a first scanning line and a second scanning line. Thus, it is also possible to reduce the number of consecutive scanning lines on which the OCT signal determined not to be proper, up to two scanning lines or less.

In the example, a configuration in which the MC image corresponding to at least any scanning line before and after the scanning line on which the OCT signal determined not to be proper has been acquired is used in interpolation processing is described as an example. However, it is not limited thereto. For example, MC images corresponding to the surrounding scanning lines on which the OCT signal determined not to be proper has been acquired may be used in interpolation processing. As an example, MC images corresponding to six scanning lines (for example, three scanning lines before and after the region B) around the region B corresponding to the scanning line on which the OCT signal determined not to be proper by the control unit 70 has been acquired may be used. In this case, the six surrounding scanning lines may be constituted by only scanning lines on which the MC image corresponding to the OCT signal determined to be proper has been acquired. If a configuration of storing even an OCT signal determined not to be proper, in the memory 74 is provided, the six surrounding scanning lines may include a scanning line on which the MC image corresponding to the OCT signal determined not to be proper has been acquired.

In the example, a configuration of performing interpolation processing using the MC image corresponding to scanning lines before and after the scanning line on which the OCT signal determined not to be proper has been acquired is described as an example. However, it is not limited thereto. The control unit 70 may perform interpolation processing using only the MC image B1$a$ corresponding to the previous scanning line or may perform interpolation processing using only the MC image B2$b$ corresponding to the subsequent scanning line. That is, the control unit 70 may perform interpolation processing using at least any MC image of before and after the region B1.

In the example, a configuration of performing copying processing using the MC images corresponding to the scanning lines before and after the scanning line on which the OCT signal determined not to be proper has been acquired is described as an example. However, it is not limited thereto. The control unit 70 may perform copying processing on the MC image B2$a$ corresponding to the previous scanning line twice, and may perform copying processing on the MC image B2$b$ corresponding to the subsequent scanning line twice. That is, the control unit 70 may perform copying processing on at least any MC image before and after the region B2.

In the example, extrapolation processing may be performed in addition to the above-described interpolation processing. As an example, in a case where the OCT signal determined not to be proper is acquired on the first scanning line (that is, the scanning line SL1 in FIG. 3B), the front face MC image of the first scanning line may be acquired by performing extrapolation processing on the front face MC image corresponding to the OCT signal determined to be proper on the next scanning line. As an example, in a case where the OCT signal determined not to be proper is acquired on the final scanning line (that is, the scanning line SLn in FIG. 3B), the front face MC image of the final scanning line may be acquired by performing extrapolation processing on the front face MC image corresponding to the OCT signal determined to be proper on the previous scanning line. That is, extrapolation processing may be applied in a case where the OCT signal acquired on a scanning line corresponding to at least one of both ends of the front face MC image. Extrapolation processing may be applied to the front face MC image corresponding to a scanning line at any position.

In the example, the ophthalmic imaging apparatus may perform tracking processing of tracing the movement of the subject eye and correcting the scanning line of the measurement light for the subject eye. For example, the movement of the subject eye is traced by repeatedly acquiring the SLO front face image with the observation optical system 200, and the scanning line of the measurement light may be corrected to the set scanning line by using such an SLO front face image. In this case, the control unit 70 may store the SLO front face image in which the scanning line of the measurement light has been set, in the memory 74 as a reference image of tracking processing. The position-shifted amount may be detected by comparing the reference image and the SLO front face image acquired as needed so as to detect an optic disc and the like. For example, the control unit 70 may detect the position-shifted amount of the subject eye E from the position of the optic disc in two SLO front face images and control driving of the scanner 108 based on the position-shifted amount. Thus, the control unit may correct the scanning line of the measurement light with respect to the optic disc. Thus, it is possible to properly scan with the measurement light even though the position of the subject eye is shifted.

For example, in a case where tracking processing is not stable, the control unit 70 may stop tracking processing and change the scanning line of the measurement light to the next scanning line. For example, whether or not tracking processing is stable may be determined from whether or not predetermined time elapses from a start of tracking, whether or not position shift of the subject eye is detected by the SLO device, and whether or not plural OCT data acquired on one scanning line includes OCT data different from other OCT data. In a case where the position of the subject eye is largely shifted, the number of OCT data determined not to be proper is large with respect to the total number of acquired OCT data. Similarly, the number of scanning lines on which OCT data determined not to be proper has been acquired is large with respect to the total number of scanning lines on which scanning with the measurement light has been performed. Therefore, the control unit 70 may determine whether or not tracking is stable, for example, from the accumulated value of OCT data determined not to be proper and the accumulated value of a scanning line on which OCT data determined not to be proper has been acquired.

For example, in the example, the OCT data on a scanning line in which tracking processing is not stable is not acquired. However, interpolation processing may be performed with using OCT data corresponding to the surrounding scanning lines of the scanning line in which the tracking processing is not stable. Thus, even in a case where tracking processing is not stable, it is possible to reduce the imaging time of a subject eye and to acquire the imaged image of the subject eye with high efficiency.

As described above, in the example, the ophthalmic imaging apparatus includes the processor that traces and detects the movement of the subject eye, and controls the scanner based on the detection result of the movement to correct the scanning line with respect to the subject eye. For example, it is possible to reduce the imaging time of the subject eye and to acquire the imaged image of the subject eye with high efficiency by determining whether or not the OCT data acquired on the scanning line is stable and changing the scanning line and by performing interpolation on the OCT data determined not to be proper in a case where the subject eye moves, and tracking is not stable.

In the example, a configuration of imaging the fundus Ef of the subject eye E with the ophthalmic imaging apparatus 1 and acquiring OCT data of the fundus Ef is described as an example. However, it is not limited thereto. For example, an examination target object may be a living body (for example, a skin and a blood vessel) other than the subject eye, and the example can be applied to an apparatus that acquires the OCT data.

1 Ophthalmic imaging apparatus
70 Control unit
74 Memory
65 SLO front face image
66 Front face motion contrast image
75 Monitor
100 OCT optical system
108 Scanner
120 Detector
200 Observation optical system
300 Fixation guidance portion

What is claimed is:

1. An ophthalmic imaging apparatus that acquires OCT data of a subject eye, comprising:
   an OCT optical system configured to detect an interference signal between measurement light with which the subject eye is irradiated and reference light;
   a scanner configured to scan with the measurement light on a scanning line on the subject eye;
   a display on which the scanning line of the measurement light is displayed; and
   a processor configured to:
   determine whether or not the OCT data acquired on the scanning line is proper;
   control the scanner based on a determination result to change the scanning line to a next scanning line; and
   interpolate an alternative to OCT data determined not to be proper, based on OCT data corresponding to a scanning line on the subject eye taken by the ophthalmic imaging apparatus during examination of the subject eye and at least either before or after a scanning line on which the OCT data determined not to be proper is acquired; and
   wherein, in a case where the OCT data determined not to be proper are consecutively acquired in scanning of a plurality of scanning lines that are different from each other, on the next scanning line that is different from the plurality of scanning lines, the processor controls the scanner to continuously scan with the measurement light until OCT data determined to be proper is acquired.

2. The ophthalmic imaging apparatus according to claim 1,
   wherein the processor
   controls the scanner to scan with the measurement light on the same scanning line a predetermined number of times, and
   changes the scanning line to the next scanning line in a case where OCT data determined to be proper is acquired or in a case where the OCT data determined not to be proper are acquired in scanning of all the predetermined number of times.

3. The ophthalmic imaging apparatus according to claim 1,
   wherein the processor interpolates the alternative to the OCT data determined not to be proper, based on OCT data determined to be proper, which is acquired in scanning on at least any one of scanning lines before and after the scanning line on which the OCT data determined not to be proper is acquired.

4. The ophthalmic imaging apparatus according to claim 1,
   wherein the processor is configured to:
   trace and detect a movement of the subject eye; and
   control the scanner based on a detection result of the movement to correct the scanning line for the subject eye,
   wherein in a case where a correction of the scanning line is not stably performed, the processor stops the control based on the detection result and changes the scanning line of the measurement light to the next scanning line.

5. The ophthalmic imaging apparatus according to claim 1,
   wherein the OCT data is motion contrast data acquired by arithmetically processing the interference signal, and
   the processor interpolates an alternative to motion contrast data determined not to be proper, based on motion contrast data of scanning lines around a scanning line on which the motion contrast data determined not to be proper is acquired.

6. The ophthalmic imaging apparatus according to claim 5, wherein the motion contrast data is front face motion contrast data corresponding to the scanning line, and the processor interpolates an alternative to front face motion contrast data determined not to be proper, based on front face motion contrast data of scanning lines around a scanning line on which the front face motion contrast data determined not to be proper is acquired.

7. A non-transitory computer readable recording medium storing an ophthalmic imaging program used in an ophthalmic imaging apparatus that includes an OCT optical system configured to detect an interference signal between measurement light with which a subject eye is irradiated and reference light, and acquires an OCT data of the subject eye by processing the interference signal, wherein the ophthalmic imaging program is executed by a processor of the ophthalmic imaging apparatus to cause the ophthalmic imaging apparatus to perform:

determining whether or not OCT data acquired on a scanning line is proper;

controlling a scanner based on a determination result to change the scanning line to a next scanning line; and interpolating an alternative to OCT data determined not to be proper, based on OCT data corresponding to a scanning line at least either before or after a scanning line on which OCT data determined not to be proper is acquired;

wherein, in a case where the OCT data determined not to be proper are consecutively acquired in scanning of a plurality of scanning lines that are different from each other, on the next scanning line that is different from the plurality of scanning lines, causes the processor to control the scanner to continuously scan with the measurement light until OCT data determined to be proper is acquired; and displaying on a screen the scanning line of the measurement light.

8. The ophthalmic imaging apparatus according to claim 1, wherein, in a case where the OCT data determined not to be proper are consecutively acquired in scanning of two of scanning lines which are different from each other, on the next scanning line, the processor controls the scanner to continuously scan with the measurement light until OCT data determined to be proper is acquired.

9. The ophthalmic imaging apparatus according to claim 1, wherein when a movement of the subject eye occurs, scanning on the next scanning line is not repeated in a case where the OCT data determined not to be proper is acquired in scanning of a scanning line, and scanning on next scanning line is repeated in a case where the OCT data determined not to be proper are consecutively acquired in scanning of a plurality of scanning lines different from each other.

* * * * *